United States Patent
Phillips et al.

(10) Patent No.: US 6,887,198 B2
(45) Date of Patent: May 3, 2005

(54) GOOSENECK SURGICAL RETRACTOR POSITIONER AND METHOD OF ITS USE

(76) Inventors: Burns P. Phillips, P.O. Box 293180, Nashville, TN (US) 37229; Larry Griffith, 17637 Kettering Trail, Lakeville, MN (US) 55044

(*) Notice: Subject to any disclaimer, the term of this patent is extended or adjusted under 35 U.S.C. 154(b) by 71 days.

(21) Appl. No.: 10/153,023

(22) Filed: May 21, 2002

(65) Prior Publication Data

US 2003/0069479 A1 Apr. 10, 2003

Related U.S. Application Data

(63) Continuation-in-part of application No. 10/117,929, filed on Apr. 5, 2002, now Pat. No. 6,733,444.
(60) Provisional application No. 60/327,437, filed on Oct. 5, 2001.

(51) Int. Cl.[7] .............................................. A61B 17/02
(52) U.S. Cl. ...................................... 600/228; 600/227
(58) Field of Search ............................... 600/201, 210, 600/213, 214, 215, 219, 220, 221, 222, 225, 226, 227, 228, 229, 230, 231, 234

(56) References Cited

U.S. PATENT DOCUMENTS

| | | | | |
|---|---|---|---|---|
| 2,594,086 A | * | 4/1952 | Smith .......................... | 600/228 |
| 3,040,739 A | * | 6/1962 | Grieshaber .................. | 600/228 |
| 3,542,015 A | * | 11/1970 | Steinman .................... | 600/217 |
| 3,858,578 A | * | 1/1975 | Milo .......................... | 600/229 |
| 4,010,741 A | * | 3/1977 | Gauthier ..................... | 600/234 |
| 4,143,652 A | * | 3/1979 | Meier et al. ................. | 600/203 |
| 4,254,763 A | * | 3/1981 | McCready et al. .......... | 600/230 |
| 4,457,300 A | * | 7/1984 | Budde ......................... | 600/228 |
| 4,617,916 A | * | 10/1986 | LeVahn et al. ............. | 600/228 |
| 4,813,401 A | * | 3/1989 | Grieshaber .................. | 600/234 |
| 4,867,404 A | * | 9/1989 | Harrington et al. .......... | 606/46 |
| 4,971,037 A | * | 11/1990 | Pelta .......................... | 600/234 |
| 5,513,827 A | * | 5/1996 | Michelson ............... | 248/279.1 |
| 5,772,583 A | * | 6/1998 | Wright et al. .............. | 600/232 |
| 5,795,291 A | * | 8/1998 | Koros et al. ................. | 600/232 |
| 5,865,730 A | * | 2/1999 | Fox et al. .................... | 600/228 |
| 5,879,291 A | * | 3/1999 | Kolata et al. ................ | 600/227 |
| 5,899,425 A | * | 5/1999 | Corey Jr. et al. ......... | 248/276.1 |
| 5,931,777 A | * | 8/1999 | Sava .......................... | 600/213 |
| 5,984,865 A | * | 11/1999 | Farley et al. ............... | 600/213 |
| 6,019,722 A | * | 2/2000 | Spence et al. .............. | 600/210 |
| 6,042,540 A | * | 3/2000 | Johnston et al. ............ | 600/213 |
| 6,206,826 B1 | * | 3/2001 | Mathews et al. ........... | 600/210 |
| 6,210,325 B1 | * | 4/2001 | Bartie et al. ................ | 600/229 |
| 6,302,843 B1 | * | 10/2001 | Lees et al. .................. | 600/228 |
| 6,361,492 B1 | * | 3/2002 | Santilli ....................... | 600/205 |
| 6,383,134 B1 | * | 5/2002 | Santilli ....................... | 600/205 |
| 6,464,634 B1 | * | 10/2002 | Fraser ........................ | 600/233 |
| 6,626,830 B1 | * | 9/2003 | Califiore et al. ............ | 600/229 |

* cited by examiner

Primary Examiner—Eduardo C. Robert
Assistant Examiner—David Comstock

(57) ABSTRACT

A gooseneck positioner secures a fixed support to one of a surgical spreader retractor and a connection head on a retractor blade. The positioner prevents the two retractor blades from riding out of an incision during a surgical operation. The gooseneck mechanism allows for the relative easy placement and then securing of the positioner at a desired location.

3 Claims, 3 Drawing Sheets

GOOSENECK SURGICAL RETRACTOR POSITIONER AND METHOD OF ITS USE

This application claims the benefit of U.S. Provisional Patent Application No. 60/327,437 filed Oct. 5, 2001, and U.S. patent application Ser. No. 10/117,929 filed Apr. 5, 2002, now U.S. Pat. No. 6,733,444.

FIELD OF THE INVENTION

The present invention relates generally to a surgical apparatus and its method of use with retractor blades and retractor blade holders to assist in retaining retractor blades at a specific location, and more particularly to prevent retractor blades from riding up out of an incision once positioned by a surgeon.

BACKGROUND OF THE INVENTION

When conducting some surgical procedures, it is often desirable to retract tissue. U.S. Pat. No. 6,042,540 shows several retractor designs which allow for top loading or side loading of retractor blades into a socket. The side loading feature of this, and other prior art, is believed to be advantageous whereby the surgeon's vision is not obscured while connecting, or disconnecting a blade from a retractor. This reference discusses the use of this socket in longitudinal retractors, and transverse retractors, as well.

The '540 patent does not contemplate two instruments retaining a single retractor blade at a given period in time. Specifically, the connector head illustrated and described is intended to be received in a single socket. Furthermore, the retractors illustrated in the reference are not described as being connectable to a stable frame such as bed rails or other secure support. While two retractor blades may be placed within an incision in a patient with this device, a problem experienced by surgeons is that one side sometimes tends to ride up and out of the wound since the incision is under tension (i.e., tends to close itself). One of the blades will often dig into its proper position, but there is a tendency in many instances for the other opposing blade to ride up out of the incision.

U.S. Pat. No. 5,513,827 shows a gooseneck adjustment member connected to a retractor blade for use in back surgery. While this device will place a single retractor blade in a fixed position, the reference does not suggest the maintenance of two retractor blades moveable relative to one another with a retractor in a desired position. Furthermore, the connection of the gooseneck adjustment member to the retractor blade itself could be improved. Also this gooseneck device does not connect to a retractor member, only to a single retractor blade.

While patents such as U.S. Pat. No. 6,234,961 are directed to retractor assemblies, this device is not a traditional retractor as the only way to retract tissue with this device without using other retractors or retractor blades is to loosen a clamp and pull the retractor blade along its shaft axis. As a practical matter this would be very difficult is the blades are already under tension spreading an incision apart.

Accordingly, a need exists for an improved method of retaining a retractor at a desired location in an incision, and a device for implementing the method.

SUMMARY OF THE INVENTION

A need exists for a gooseneck surgical instrument and method of it use which accepts a retractor blade connection while a retractor is still connected to the blade.

Another need exists for a surgical retractor to be connected to a stabilizing apparatus securely connected to a fixed support such as a rail of a surgical operating bed.

Another need exists for a side loading surgical retractor and an improved connector head attached to retractor blades where the surgical retractor may be connected to two retractor blades at the connector heads and a stabilizing gooseneck apparatus may be connected to at least one of the retractor blades or surgical retractor to hold the retractor blades in position.

Yet another need exists for a stabilizing apparatus which is easily and quickly moved into position and then locked into position securing a plurality of retractor blades at a specific spatial orientation.

Accordingly, a positioner, such as a gooseneck retaining mechanism, is provided for use in surgical operations which may be secured to a fixed support at a first end. A second end of the gooseneck retaining mechanism preferably connects to a connection head on a retractor blade as described in copending application No. 60/327,437, incorporated by reference. A surgical retractor, such as the one described in U.S. patent application Ser. No. 10/117,929, also incorporated by reference, is also attached to the connection head and the surgical retractor retains a second retractor blade in position relative to the first retractor blade in a relatively rigid spatial orientation to prevent at least one, and preferably both of the blades from riding out of the incision.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
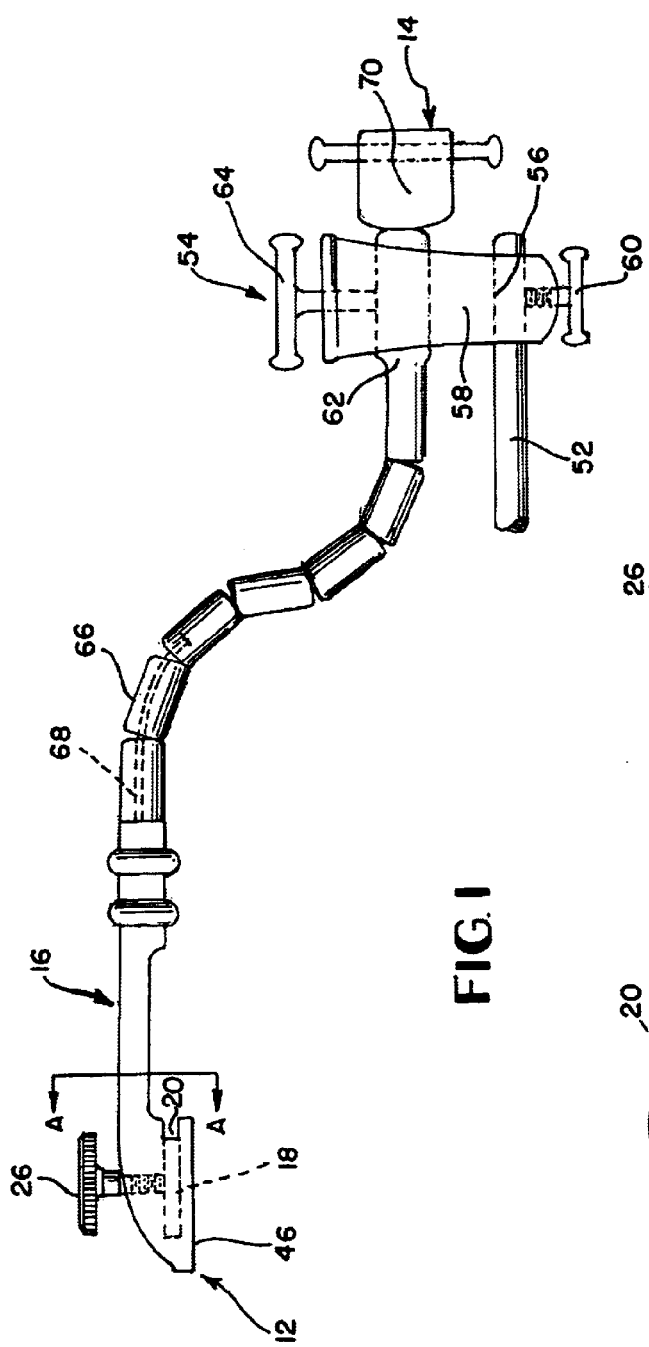
FIG. 1 is a side plan view of a gooseneck positioning apparatus of the present invention with selected interior portions illustrated in phantom.
Figure 3:
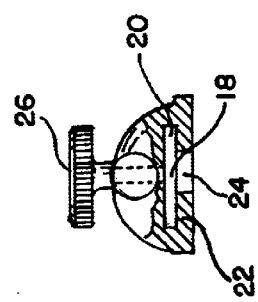
FIG. 3 is a back plan view of the first connection end shown in FIG. 2 taken along the line a—a shown in FIG. 1.
Figure 2:
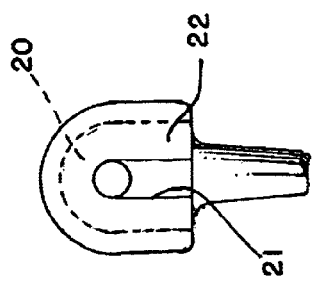
FIG. 2 is a bottom view of a first connection end of the gooseneck positioning apparatus of FIG. 1 with selected interior portions illustrated in phantom.

FIG. 1 illustrates a preferred embodiment of a positioner 10, illustrated as a gooseneck positioner, having a first end 12 and a second end 14. The first end 12 has a connector 16 with a socket 18. The socket 18 has a slot 20 above a ledge 22 about an opening 24. The opening allows for a post of a connection head to be inserted into the socket while receiving a cap into the slot 20. A retainer 26, a screw is illustrated, may positively lock the connection head to the first end of the positioner 10.

Figure 4:
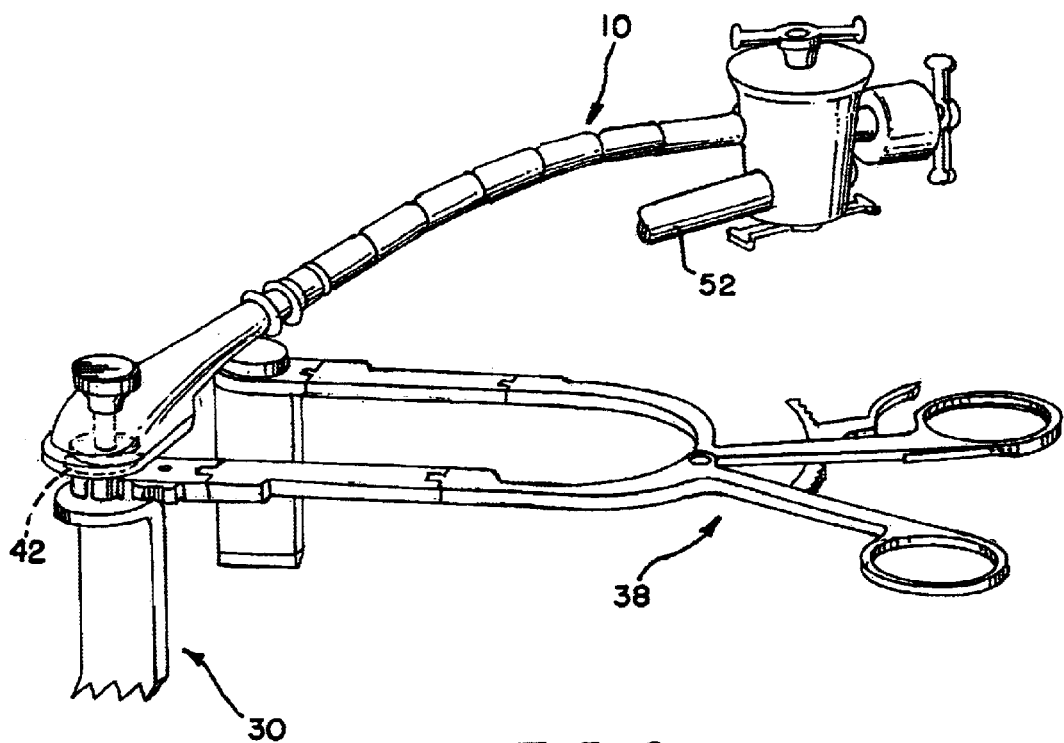
FIG. 4 is a top perspective view showing the gooseneck positioning apparatus together with a surgical retractor and two retractor blades.
Figure 7:
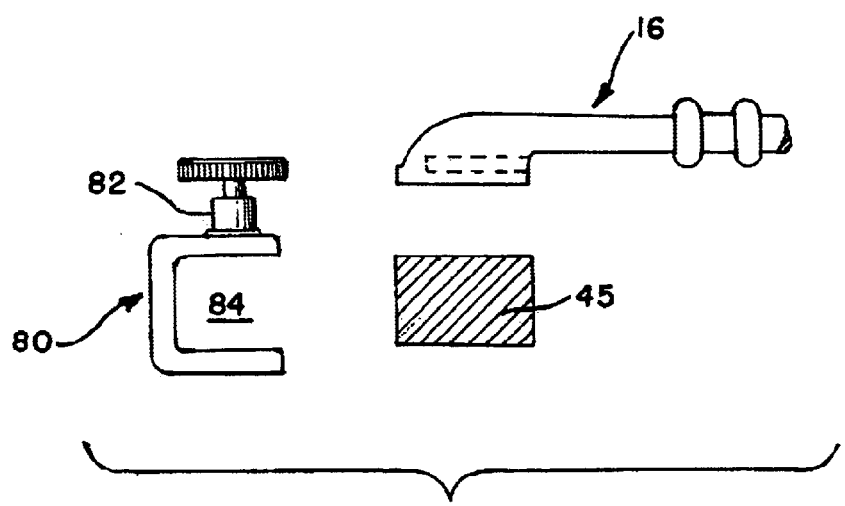
FIG. 7 is a side cross-sectional view of an alternative connection for retaining the gooseneck positioning apparatus to a retractor.
Figure 6:
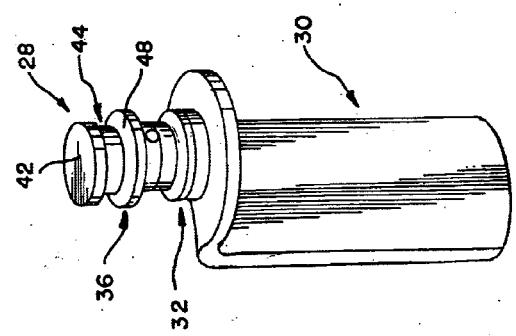
FIG. 6 is a top perspective view of the retractor blade and connection head utilized in FIG. 4.
Figure 5:
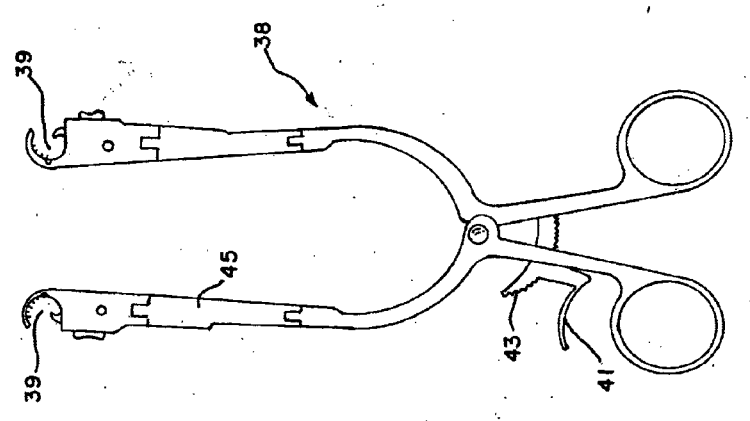
FIG. 5 is a top plan view of the retractor shown in FIG. 4.

Reference to FIG. 6 is helpful to see the connection of the connector 16 with a connection head 28 on a retractor blade 30 as shown in FIG. 4. The connection head 28 has two loading portions 32,34 separated by cap 36. The first loading portion 32 may be utilized by the connector 16 of the positioner 10. Of course, if the connector 16 were designed in another manner, the second loading portion 34 could possibly be utilized with the connector 16 as shown in FIG. 4. Other connection heads 28 may not have a cap 36 separating loading portions 32,34. The connection head 28 is a male fitting while the socket 20 is a female fitting. Other designs could have a male fitting on the connector 16 and a female fitting on the retractor blade 30. Furthermore, other designs may employ multiple fittings on the retractor blade 30 or have one or more fittings on a retractor, such as on retractor 38 shown in FIG. 5, or connect the positioner 10 to the retractor 38 as illustrated in FIG. 7.

Retractors 38 as defined herein have the ability to allow an operator to move one retractor blade relative to another retractor blade and then maintain a desired spacing therebetween. Typically, this is done by moving the retainers 39 or fittings on the retractor 38 which hold the retractor blades. This typically results in substantially linear movement of the blades apart from one another as the blades are often adapted to rotate within the retainer 39. Retractors 38 typically have a first configuration which allows only one way spreading of the blades 30. Typically this is accomplished through a ratchet mechanism which prevents movement in an opposing direction. This allows the doctor to spread tissue and then retain it in an open configuration. The illustrated retractor 38 has a locking member 41 which allows spreading of the blades 30 in the first configuration. A second configuration moves the locking member 41 out of engagement with toothed hub 43 to allow two way movement, such as to release the retractor 38.

In the preferred embodiment, the top 42 of the connection head 28 is received in slot 20 while post 44 passes into opening 24. The top 42 rests on ledge 22 and retainer 26 secures the top 42 within the slot 20. In this configuration, the blade 30 is connected to the gooseneck positioner 10. Furthermore, as illustrated in FIG. 4, the surgical retractor 38 is also connected to the connection head 28 and to the gooseneck positioner 10.

A bottom surface 46 of the connector 16 rests against a top surface 48 of the cap 36. A bottom surface of the cap 36 may rest against a top surface of the retractor 38 with the second loading Portion 34 of the connection head 28 retained within a socket 39 of the retractor 38. When two retractor blades 30 are held in two sockets 39 of the retractor 38, the gooseneck positioner 10 provides stability to both blades 30. In other embodiments, the gooseneck positioner may connect to other fittings than the connection head 28 used by the retractor 38, or may connect directly to the retractor 38 to retain the retractor 38 in a fixed position relative to a support 52. The support 52 may be a bed rail, or other support structure which provides rigidity to the blades 30 and retractor 38.

The positioner 10 has a second end 14 with a clamp 54 which secures the positioner 10 to the support 52. The clamp 54 may allow for rotational adjustment of the clamp 54 about a cylindrical support as well as longitudinal placement of the clamp 54 on the support 52 such as by utilizing a bore 56 within a housing 58. A stop 60, such as a threaded bolt engages the shaft 52 to secure the clamp 54 relative to the shaft 52.

The clamp 54 may also utilize similar retaining mechanism as illustrated to secure the positioner 10 relative to the clamp 54 as illustrated. This configuration allows the clamp 54 to be fixed at a desired location on the support 52 and the positioner 10 to then be located where desired. Rotational positioning of the base 62 of the positioner 10 is provided in the preferred embodiment with stop 64.

The preferred positioner 10 has a gooseneck linkage system 66 and may operate similarly to the linkage system illustrated in U.S. Pat. No. 5,513,827, or otherwise. An internal cable 68 may be tightened with tightener 70 to make the linkage system 66 at least relatively rigid. It is anticipated that upon operation of the tightener 68, the linkage system will secure the connector 16 at a specific location relative to an incision and be operatively connected to a retractor blade 30 and/or a surgical retractor 38. Other positioners other than gooseneck positioners may also be utilized in other embodiments.

The tightener 70 may be constructed in many different ways. One way to construct an operative tightener 70 is to have a hollow portion in the base 62 and a shaft extending into the hollow portion of the base from the tightener 70. Threads on both the hollow portion and the shaft allow for the tightener 70 to be moved toward and away from the base upon rotation of the tightener 70. The internal cable 68 may be connected to the tightener 70 so that when the tightener 70 moves away from the base 62, the individual linkages are pulled together so that their special relationship relative to one another is not easily moved.

In operation, it is likely that a surgeon will make an incision and then utilize the retractor 38 with blades 30 connected thereto at the second loading portions 34 to spread the tissue and retain the tissue spread. The clamp 54 is, or has been, appropriately located on a support 52 and the linkage system 66 will be moveable to allow positioning of the connector 16. Once the connector 16 is appropriately located, the tightener 68 may be operated to secure the position of the linkage system 66, either before or after attachment of the connector 16 to the connection head 28 or to the retractor 38. In the preferred embodiment, the connector 16 will then be connected to the surgical retractor 38, such as at one of the first loading portions 32 of the connection head 28 on one of the retractor blades 30 into a receiver 39 on the retractor 38. Of course, the sequence of events may be altered, but it is anticipated that the positioner 10 will be utilized to provide a rigid support for the surgical retractor 38 with the blades 30 in position within an incision to prevent one or both of the blades 30 from riding up out of the incision.

FIG. 7 shows a holder 80 which may be utilized to connect the connector 16 to the retractor 38. Specifically, the retractor arm 45 shown in FIG. 5 and in cross section FIG. 7 may be grasped by holder 80 instead of directly connecting the connector 16 to the connection head 28. The holder 80 is illustrated with a connection head 82 which is grasped by the connector 16. The holder 80 also has a channel 84 which receives the retractor frame arm 45 therein to restrict the retractor arm 45 so as to hold the retractor 38 in a desired position to prevent either one of the retractor blades 30 from riding up out of an incision. The U-shaped holder is the preferred design for a holder 80, but other holders or connections could also be utilized to directly retain the retractor 38 with the positioner 10 in a desired location to prevent at least one of the blades 30 from riding up and out of the incision inadvertently.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A surgical technique comprising the steps of:
   spreading tissue with a surgical retractor having at least two retractor blades and maintaining the tissue spread with the retractor, said blades being connected to the retractor throughout the spreading of tissue;
   connecting at least one of the surgical retractor and retractor blades to a positioner having a first end and a second end, a connector at the first end connected to the at least one of the surgical retractor and retractor blades, and a clamp at the second end securing the positioner to a support, said first end moveable in a first configuration; and
   placing the positioner in a second configuration securing the first end relative to the second end in a rigid configuration;
   wherein the spreading of tissue is performed before connecting the positioner to the at least one of the surgical retractor and retractor blades.

2. The surgical technique of claim 1 wherein the positioner is in the first configuration when connected to the at least one of the surgical retractor and retractor blades.

3. The surgical technique of claim 1 wherein the positioner is a gooseneck positioner having moveable linkages in the first configuration which allows movement during the connecting of the positioner to the at least one of the surgical retractor and retractor blades and the linkages are secured relative to one another in the second configuration.

* * * * *